United States Patent
Mondal et al.

(10) Patent No.: US 9,540,292 B2
(45) Date of Patent: Jan. 10, 2017

(54) PROCESS FOR NON-OXIDATIVE DEHYDROGENATION OF ALKANE

(71) Applicant: SAUDI BASIC INDUSTRIES CORPORATION, Riyadh (SA)

(72) Inventors: Kartick Chandra Mondal, Gujarat (IN); Himanshu Patel, Gujarat (IN)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 14/709,972

(22) Filed: May 12, 2015

(65) Prior Publication Data

US 2015/0238933 A1    Aug. 27, 2015

Related U.S. Application Data

(62) Division of application No. 13/901,598, filed on May 24, 2013, now Pat. No. 9,120,714.

(51) Int. Cl.
| | |
|---|---|
| *C07C 5/333* | (2006.01) |
| *B01J 23/22* | (2006.01) |
| *B01J 37/04* | (2006.01) |
| *B01J 37/08* | (2006.01) |
| *B01J 21/06* | (2006.01) |
| *B01J 23/00* | (2006.01) |

(52) U.S. Cl.
CPC ............ *C07C 5/3332* (2013.01); *B01J 21/066* (2013.01); *B01J 23/002* (2013.01); *B01J 23/22* (2013.01); *B01J 37/04* (2013.01); *B01J 37/08* (2013.01); *B01J 37/088* (2013.01); *B01J 2523/00* (2013.01); *C07C 2521/06* (2013.01); *C07C 2523/22* (2013.01); *Y02P 20/52* (2015.11)

(58) Field of Classification Search
CPC ................................ B01J 21/066; B01J 23/22
USPC .................................................. 502/349, 353
See application file for complete search history.

(56) References Cited

U.S. PATENT DOCUMENTS

| | | | |
|---|---|---|---|
| 6,198,005 B1 * | 3/2001 | Wachs | .................... C07C 45/27 |
| | | | 423/415.1 |
| 8,465,713 B2 * | 6/2013 | Schermanz | ........ B01D 53/9418 |
| | | | 423/239.1 |
| 2005/0038299 A1 * | 2/2005 | Wachs | ................... B01J 23/002 |
| | | | 568/472 |

FOREIGN PATENT DOCUMENTS

| | | | | |
|---|---|---|---|---|
| CN | 10-3121715 | * | 5/2013 | ............. C10G 31/00 |
| CN | 10-3641170 | * | 3/2014 | ............. C10G 31/00 |
| NL | WO 2013174866 A1 | * | 11/2013 | ............. B01J 23/22 |

OTHER PUBLICATIONS

"Propane oxidative dehydrogenation on VOx/ZrO2 catalysts," C. L. Pieck et al. Journal of Catalysis 224 (2004), pp. 1-7.*

(Continued)

*Primary Examiner* — Patricia L Hailey

(74) *Attorney, Agent, or Firm* — Cantor Colburn LLP

(57) ABSTRACT

The invention relates to a process for preparing a catalyst composition comprising an unsupported catalyst comprising $ZrV_2O_7$, comprising: mixing ammonium meta-vanadate and zirconyl nitrate, drying the mixture and calcining the dried mixture at a temperature range of 600-900° C. for 2-10 hours to obtain the unsupported catalyst, and mixing the unsupported catalyst with $Al_2O_3$ without heating.

14 Claims, No Drawings

(56) References Cited

OTHER PUBLICATIONS

"Structural, negative thermal expansion and photocatalytic properties of ZrV2O7: a comparative study between fibers and powders," Qinqin Liu et al. Materials Characterization 96 (2014), pp. 63-70.*

"Surface acidic and redox properties of V—Zr—O catalysts for the selective oxidation of toluene to benzaldehyde," Jiazhen Ge et al. Journal of Molecular Catalysis A: Chemical 278 )2007), pp. 209-214.*

European Search Report for European Patent Application No. 12004056.3; European Filing Date: May 24, 2012. 7 Pages.

Gazzoli et al. "Bulk and Surface Structures of V2O5/ZrO2 Catalysts for n-butane Oxidative Dehydrogenation", Journal of Molecular Catalysis A: Chemical; vol. 310, Issues 1-2, 1 (2009); pp. 17-23.

Harlin et al. "Effect of Mg and Zr Modification on the Activity of VOx/Al2O3 Catalysts in the Dehydrogenation of Butanes", Journal of Catalysis; vol. 203, No. 1, Oct. 1, 2001, pp. 242-252(11).

International Search Report and Written Opinion of the International Searching Authority for PCT/EP2013/060508 mailed Oct. 21, 2013, 13 pages.

Khodakov et al. "Structure and Properties of Vanadium Oxide-Zirconia Catalysts for Propane Oxidative Dehydrogenation", Journal of Catalysis; vol. 177, Issue 2, (1998); pp. 343-351.

Partial European Search Report for European Patent Application No. 12004056.3; European Filing Date: May 24, 2012, 6 Pages.

Shah et al. "Comparison of Redox Isotherms for Vanadia Supported on Zirconia and Titania", Applied Catalysis A: General; vol. 361, Issues 1-2, Jun. 20, 2009, pp. 13-17.

Extended European Search Report for European Application No. 16162938.1; Date of Mailing: Jul. 19, 2016; Date of Completion: Jul. 13, 2016; 8 Pages.

Lorenzo Fabian-Mijangos et al: "V Loading 1-5 Effect on V2O5/ZrO2 Catalysts for Oxidative Desulfurization", Industrial & Engineering Chemistry Research, vol. 50, No. 5, Mar. 2, 2011, pp. 2659-2664.

Prangya Parimita Sahoo et al: "Synthesis, Structure, Negative Thermal Expansion, and Photocatalytic Property of Mo Doped ZrV2O7", Inorganic Chemistry, vol. 50, No. 18, Sep. 19, 2011, pp. 8774-8781.

Daqin, Y. "Composite materials having low thermal expansion and high thermal conductivity for electronic packaging—Investigation on the prepareation and basic characteristics of ZrV2O7 and ZrV2O7/A1 of composite materials" China Doctoral/Master High Quality Dissertation full text database (Master) Engineering Technology I Serial, Jul. 15, 2005, Issue 3, pp. 33 and 34.

* cited by examiner

PROCESS FOR NON-OXIDATIVE DEHYDROGENATION OF ALKANE

CROSS REFERENCE TO RELATED APPLICATIONS

This application is a divisional of U.S. application Ser. No. 13/901,598, filed May 24, 2013, which claims priority to European Application No. 12004056.3, filed May 24, 2012, which are both incorporated herein by reference in their entirety.

The present invention relates to a process for producing an alkene by the non-oxidative dehydrogenation of an alkane.

Isobutene is produced by the dehydrogenation of isobutane and as a by-product from fluid catalytic cracking (FCC) and steam cracking operations. The major application of isobutene is as feed stock in the manufacture of Methyl-tert-butyl-ether (MTBE) and production of polymers like butylrubber, polybutene and isoprene. Chromia/Alumina catalysts are typically used for the production of isobutene from isobutane.

Disposal of this catalyst poses a problem due to environmental regulations and involves major expenditure, since chromium is a known carcinogen. Chromium exists in two stable oxidation states, namely +3 and +6. In general, chromium (VI) is more toxic than chromium (III). Long-term exposure to chromium has been associated with lung cancer in workers exposed to levels in air that were 100 to 1,000 times higher than those found in the natural environment. One of the safe methods of disposal is to reclaim Cr from the spent catalyst for reuse and then dispose the catalyst. However, the reclaiming of Cr from the catalyst is not feasible. Some of the other ways the waste catalyst can be disposed are by use in cement bricks, use in steel industry and in refractory industry. To overcome these problems, development of non-chromia catalyst is essential.

There has been an ongoing research for non-chromium catalyst for the production of isobutene by the non-oxidative dehydrogenation of isobutane, which matches the performance of the chromia catalyst with respect to conversion, selectivity and catalyst life.

Harlin et. al., Journal of Catalysis 203, 242-252 (2001) describes the use of vanadium oxide catalyst modified by Zr supported on alumina in a non-oxidative dehydrogenation process of isobutane. The catalyst was prepared by the incipient wetness impregnation method with alumina as the support. The catalyst was prepared by applying an aqueous solution of $ZrO(NO_3)_2 \cdot 7H_2O$ and an aqueous solution of $NH_4VO_3$ to alumina particles and drying and calcining the particles. The catalyst comprises $\gamma$-$Al_2O_3$, $ZrO_2$ and a minor amount of $ZrV_2O_7$. The isobutane feed was diluted with nitrogen ($N_2$:Isobutane=9:1).

There is a continuous need in the art for a process which results in a higher conversion rate of isobutane and selectivity to isobutene.

Accordingly, the present invention provides a process for producing an alkene by non-oxidative dehydrogenation of an alkane, comprising contacting a feed stream comprising the alkane with a catalyst composition comprising an unsupported catalyst comprising $ZrV_2O_7$ at a temperature of 400 to 600° C.

Surprisingly, the process according to the present invention shows a high conversion rate and a high selectivity.

It is noted that Khodakov et. al., Journal of Catalysis, 343-351 (1998) mentions the use of bulk $ZrV_2O_7$ prepared from a stoichiometric mixture of $V_2O_5$ and $ZrO_2$ for a dehydrogenation process of isobutane. The dehydrogenation process in this publication is an oxidative dehydrogenation process. Bulk $ZrV_2O_7$ did not show catalytic effects. This publication also mentions the use of vanadium oxide catalysts supported on zirconia in an oxidative dehydrogenation process of isobutane.

As used herein, the term "non-oxidative dehydrogenation" is understood to mean that the dehydrogenation proceeds substantially in the absence of an oxidizing agent such as oxygen, i.e. the amount of the oxidizing agent in the feed stream is at most 5 vol %.

A supported catalyst is typically prepared by applying a solution of the active component to a material having a larger surface area and drying and calcining the material. As used herein, the term 'unsupported catalyst' is understood to mean that the catalyst is not deposited on a material by a process involving calcination. When the catalyst is mixed with a further material without heating, said further material is understood to be not a catalyst support, and the catalyst in the resulting composition remains as an unsupported catalyst.

As used herein, the term "catalyst composition" is understood to mean a composition consisting of the catalyst (active phase) and any other suitable components such as a catalyst binder.

Preferably, said alkene is selected from the group consisting of ethylene, propylene, n-butene, isobutene, 1,3-butadiene and mixtures thereof and said alkane is selected from the group consisting of ethane, propane, n-butane, isobutane, and mixtures thereof. Most preferably, the process according to the invention is a process for producing isobutene from isobutane.

Preferably, the catalyst comprises $ZrV_2O_7$ as a major phase. Accordingly, the catalyst comprises at least 30 wt % of $ZrV_2O_7$. More preferably, the catalyst comprises at least 40 wt %, at least 50 wt %, at least 60 wt %, at least 70 wt %, at least 80 wt %, at least 90 wt %, more preferably at least 95 wt %, even more preferably at least 99 wt %, of $ZrV_2O_7$.

Preferably, the feed stream comprises at least 80 vol % of the alkane, preferably at least 90 vol %, more preferably at least 95 vol %, even more preferably at least 99 vol %, of the alkane. Accordingly, the process is performed with little or no amount of feed diluents. This has an advantage of eliminating the downstream diluents separation step which lead to the reduction of overall operation cost. The throughput for a given size of reactor is increased.

Preferably, the contacting step is performed at a temperature of at most 560° C., preferably at 540-560° C., around 550° C. This has an advantage that the required energy for the process is low.

Preferably, the unsupported catalyst used in the process according to the present invention has been prepared by a process comprising the steps of: mixing ammonium meta-vanadate and zirconyl nitrate, drying the mixture and calcining the dried mixture at a temperature of 600-900° C. for 2-10 hours, preferably 650-850° C. for 4-6 hours, more preferably 700-750° C. for 4 h.

Preferably, ammonium meta-vanadate and zirconyl nitrate are mixed at a molar ratio between V and Zr of 0.4:1-1.3:1, preferably 0.5:1-1.1:1, more preferably 0.9:1-1.1:1. This leads to the formation of a higher proportion of $ZrV_2O_7$ in the resulting catalyst and a better performance of the catalyst.

The catalyst composition may substantially consist of the catalyst, i.e. the catalyst may be used in the process according to the invention without mixing the catalyst with other components. However, preferably, the catalyst composition used in the process of the invention may be prepared by mixing the catalyst with a catalyst binder, such as $Al_2O_3$. The mixing of the catalyst with $Al_2O_3$ is performed without heating, so that no phase change of $Al_2O_3$ occurs. The catalyst composition prepared in this way shows a high isobutane conversion rate and a higher isobutene selectivity. $Al_2O_3$ may be $\alpha$-$Al_2O_3$ or $\gamma$-$Al_2O_3$. $\gamma$-$Al_2O_3$ is more preferred since the isobutane conversion rate is higher.

The weight ratio between the catalyst and $Al_2O_3$ may be between 0.2:1 to 5:1, more preferably 0.5:1 to 2:1, more preferably 0.9:1 to 1.1:1.

According to a further aspect of the present invention, a process is provided for preparing a catalyst composition comprising an unsupported catalyst comprising $ZrV_2O_7$, comprising the steps of: mixing ammonium meta-vanadate and zirconyl nitrate, drying the mixture and calcining the dried mixture at a temperature range of 600-900° C. for 2-10 hours to obtain the unsupported catalyst and mixing the unsupported catalyst with $Al_2O_3$ without heating.

A further aspect of the present invention provides the catalyst composition obtainable by the process according to the present invention.

It is noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The present invention is illustrated below by referring to the following non-limiting experiments.

EXPERIMENTS

Comparative Experiment $\gamma$-$Al_2O_3$ supported catalyst was prepared by incipient wet impregnation method Ammonium meta-vanadate and zirconyl nitrate were mixed together to form a solution in the presence of deionized water such that the molar ratio between V and Zr were 1:1. 5 g of $\gamma$-$Al_2O_3$ was taken in a silica crucible and placed on the hot plate. The mixed solution of ammonium meta-vanadate and zirconyl nitrate was then added dropwise with stirring until the whole mass was dry. Temperature of the hot plate was kept at a temperature of 100° C. to evaporate excess water. Subsequently the dried mass was heated at a temperature of 800° C. for 4 h. A supported catalyst of $ZrV_2O_7$ supported on $\gamma$-$Al_2O_3$ was obtained.

The supported catalyst was mixed with $\gamma$-$Al_2O_3$ at 1:1 wt ratio. The mixture was crushed and sieved to a particle size of 250-500 micron. A catalyst composition comprising a supported catalyst ($ZrV_2O_7$ supported on $\gamma$-$Al_2O_3$) and a catalyst binder ($\gamma$-$Al_2O_3$) was obtained.

Isobutane was contacted with the catalyst composition obtained in a non-oxidative atmosphere in the absence of any feed diluents at a temperature of 550° C. The results are shown in Table 1.

Example 1

Ammonium meta-vanadate and zirconyl nitrate were mixed together such that the molar ratio between V and Zr were 1:1. During the mixing a very minimum quantity of water was added. The whole mass was then dried and calcined at 800° C. for 4 h to obtain a non-supported catalyst comprising $ZrV_2O_7$.

The non-supported catalyst was mixed with $\gamma$-$Al_2O_3$ at 1:1 wt ratio. The mixture was crushed and sieved to a particle size of 250-500 micron. A catalyst composition comprising a non-supported catalyst ($ZrV_2O_7$) and a catalyst binder ($\gamma$-$Al_2O_3$) was obtained.

Isobutane was contacted with the catalyst composition obtained in a non-oxidative atmosphere in the absence of any feed diluents at a temperature of 550° C. The results are shown in Table 1.

Example 2

Example 2 was repeated, except that $\gamma$-$Al_2O_3$ was replaced by $\alpha$-$Al_2O_3$. The results are shown in Table 1.

| Catalyst composition | Isobutane conversion (%) | Isobutene selectivity (%) | Isobutene yield (%) |
|---|---|---|---|
| Comp. Ex | 28.9 | 65.9 | 19.0 |
| Ex. 1 | 41 | 92 | 37.7 |
| Ex. 2 | 37 | 93 | 34.4 |

It can be seen that the non-supported catalyst leads to a higher isobutane conversion, isobutene selectivity and isobutene yield.

It can also be seen that the catalyst composition comprising $\gamma$-$Al_2O_3$ leads to a higher isobutane conversion and isobutene yield as compared to the catalyst composition comprising $\alpha$-$Al_2O_3$ while the isobutene selectivity is comparable.

The invention claimed is:

1. A process for preparing a catalyst composition comprising an unsupported catalyst comprising $ZrV_2O_7$, comprising:
   mixing ammonium meta-vanadate and zirconyl nitrate,
   drying the mixture and calcining the dried mixture at a temperature range of 600-900° C. for 2-10 hours to obtain the unsupported catalyst, and
   mixing the unsupported catalyst with $Al_2O_3$ without heating,
   wherein
     the ammonium meta-vanadate and the zirconyl nitrate are mixed at a molar ratio between V and Zr of 0.4:1-1.3:1,
     and/or
     the catalyst comprises at least 30 wt % of the $ZrV_2O_7$, based upon a total weight of the catalyst.

2. The process according to claim 1, wherein the ammonium meta-vanadate and the zirconyl nitrate are mixed at the molar ratio between the V and the Zr of 0.9:1-1.1:1.

3. The process according to claim 1, wherein the ammonium meta-vanadate and the zirconyl nitrate are mixed at the molar ratio between the V and the Zr of 0.5:1-1.1:1.

4. The process according to claim 1, wherein a weight ratio between the unsupported catalyst and the $Al_2O_3$ is between 0.2:1 to 5:1.

5. The process according to claim 1, wherein the catalyst comprises at least 50 wt % of the $ZrV_2O_7$.

6. The process according to claim 1, wherein the catalyst comprises at least 70 wt % of the $ZrV_2O_7$.

7. The process according to claim 1, wherein the catalyst comprises at least 99 wt % of the $ZrV_2O_7$.

8. The process according to claim 1, wherein the calcining is at a temperature of 650-850° C. for 4-6 hours.

9. The process according to claim 8, wherein the ammonium meta-vanadate and the zirconyl nitrate are mixed at the molar ratio between the V and the Zr of 0.9:1-1.1:1.

10. The process according to claim 9, wherein a weight ratio between the catalyst and the $Al_2O_3$ is between 0.2:1 to 5:1.

11. The process according to claim 8, wherein the ammonium meta-vanadate and the zirconyl nitrate are mixed at the molar ratio between the V and the Zr of 0.5:1-1.1:1.

12. The process according to claim 1, wherein the calcining is at a temperature of 700-750° C. for 4 h.

13. The process according to claim 1, wherein the $Al_2O_3$ is γ-$Al_2O_3$.

14. A catalyst composition obtained by the process according to claim 1.

* * * * *